US007805187B2

(12) United States Patent
Särkelä et al.

(10) Patent No.: US 7,805,187 B2
(45) Date of Patent: Sep. 28, 2010

(54) MONITORING OF THE CEREBRAL STATE OF A SUBJECT

(75) Inventors: Mika Särkelä, Helsinki (FI); Satu Jääskeläinen, Piispanristi (FI); Jaakko Långsjö, Seinäjoki (FI); Anu Maksimow, Turku (FI); Elina Salmi, Turku (FI); Harry Scheinin, Piispanristi (FI)

(73) Assignee: The General Electric Company, Helsinki (FI)

( * ) Notice: Subject to any disclaimer, the term of this patent is extended or adjusted under 35 U.S.C. 154(b) by 1480 days.

(21) Appl. No.: 11/176,969

(22) Filed: Jul. 7, 2005

(65) Prior Publication Data

US 2007/0010795 A1  Jan. 11, 2007

(51) Int. Cl.
*A61B 5/04* (2006.01)
(52) U.S. Cl. .................................. 600/544
(58) Field of Classification Search ............ 600/544, 600/545
See application file for complete search history.

(56) References Cited

U.S. PATENT DOCUMENTS 6,317,627 B1 * 11/2001 Ennen et al. ............ 600/544
6,801,803 B2 10/2004 Viertiö-Oja
2003/0055355 A1 * 3/2003 Viertio-Oja ............ 600/544

FOREIGN PATENT DOCUMENTS

EP 1 563 789 8/2005

OTHER PUBLICATIONS

"Increase in high frequency EEG activity explains the poor performance of EEG spectral entropy monitor during S-ketamine anesthesia", Maksimow et al., Clinical Neurophysiology 117 (2006) 1660-1668.
*Comparative effects of ketamine on Bispectral Index and spectral entropy of the electroencephalogram under sevoflurane anaethesia*, P. Hans et al., British Journal of Anaesthesia 94 (3): 336-40 (2005).
*Bispectral analysis of the electroencephalogram does not predict responsiveness to verbal command in patients emerging from xenon anaesthesia*, T. Goto et al., British Journal of Anaesthesia 85 93): 359-63 (2000).
*The effect of ketamine on clinical endpoints of hypnosis and EEG variables during propofol infusion*, T. Sakai et al., Acta Anaesthesiol Scand 1999; 43: 212-216.
*A comparison of bispectral index and ARX-derived auditory evoked potential index in measuring the clinical interaction between ketamine and propofol anaesthesia*, H. E. M. Vereecke et al., Anaesthesia, 2003, 58, pp. 957-961.

* cited by examiner

*Primary Examiner*—Charles A Marmor, II
*Assistant Examiner*—Christian Jang
(74) *Attorney, Agent, or Firm*—Andrus, Sceales, Starke & Sawall, LLP

(57) ABSTRACT

The invention relates to a method and apparatus for monitoring the anesthetic state of a subject. Physiological signal data including EEG and possibly also EMG signal components is acquired from a subject and supplied to a monitoring process configured to derive, based on the said data, a state index indicative of the anesthetic state of the subject. In order to extend the applicability of present-day monitoring processes, the operation of the monitoring process is controlled according to whether at least one drug inducing high frequency EEG signal components is administered to the subject. The presence of the high frequency EEG signal components in the physiological signal data may be detected automatically.

16 Claims, 3 Drawing Sheets

MONITORING OF THE CEREBRAL STATE OF A SUBJECT

FIELD OF THE INVENTION

The present invention relates generally to the monitoring of the cerebral state of a subject. The invention finds a typical application in processes monitoring the extent of a hypnotic state of a patient in connection with anesthesia or sedation.

BACKGROUND OF THE INVENTION

Neuromonitoring is a subfield of clinical patient monitoring focused on measuring various aspects of brain function and on changes therein caused by drugs commonly used to induce and maintain anesthesia in an operation room or sedation in patients under critical or intensive care.

Electroencephalography (EEG) is a well-established method for assessing brain activity. When measurement electrodes are attached on the skin of the skull surface, the weak biopotential signals generated in the pyramid cells of the cortex may be recorded and analyzed. The EEG has been in wide use for decades in basic research of the neural systems of the brain as well as in the clinical diagnosis of various central nervous system diseases and disorders.

Electromyography (EMG) is a method for recording electrical biopotentials of muscles. In an EMG measurement, the electrodes are attached onto the surface of the skin overlying a muscle. When a biopotential signal is recorded from the forehead of a subject, the recorded signal indicates both the activity of the facial muscles (fEMG) and the brain (EEG).

One of the special applications of the EEG, which has received attention recently, is the use of a processed EEG signal for objective quantification of the amount and type of brain activity for the purpose of determining the level of consciousness of a patient. In its simplest form, the utilization of an EEG signal allows the automatic detection of the alertness of an individual, i.e. if he or she is awake or asleep. This has become an issue of increased interest, both scientifically and commercially, in the context of measuring the depth of unconsciousness induced by anesthesia during surgery.

Another important component of balanced anesthesia is analgesia which means prevention of pain reactions of a patient by administration of pain medication. Adequate analgesia reduces surgical stress and there is firm evidence that it decreases postoperative morbidity. Awareness during surgery with insufficient analgesia may lead to a post-traumatic stress disorder. Low quality pre- and intra-operative analgesia makes it difficult to select the optimal pain management strategy later on. More specifically, it may cause exposure to unwanted side effects during the recovery from the surgery. If the anesthesia is too light and involves insufficient hypnosis, it may cause traumatic experiences both for the patient and for the anesthesia personnel. From an economical point of view, if the anesthesia is too deep, it may cause increased perioperative costs through extra use of drugs and time, and extend the time required for post-operative care.

Virtually every patient being cared for in an Intensive Care Unit, for example, receives some form of sedation. However, the control of the depth of the sedation administered to a patient is still problematic, and therefore oversedation and undersedation are both common occurrences in intensive care units. At present, monitoring the level of sedation is mainly handled by using subjective observations from the patient. Various sedation assessment scales have been developed for subjectively assessing the level of sedation, the Ramsay Score being one of the most widely used tools for this purpose. Inappropriate sedation can lead to an adverse clinical outcome and reduce treatment efficacy in critical care settings. Oversedation may cause various complications, such as cardiovascular instability, and it may also increase the length of stay in the hospital and prolong the usage time of expensive facilities, such as the intensive care unit. Undersedation, in turn, may result in patient anxiety and agitation, which can further interfere with care, especially with that of neurological patients, and result in harm to the patient and the nursing staff.

In connection with anesthesia, the patient is administered hypnotic, analgesic, and neuromuscular blocking agents. However, a certain drug is not normally a pure hypnotic or a pure analgesic, but the drugs normally have additive effects. The anesthetics, i.e. drugs used to produce anesthesia, may also be divided into different groups according to the site of their action. This is discussed briefly in the following.

Glutamate is the most important excitatory transmitter in the central nervous system. Glutamate is involved in sensory processing, motor control, and higher cortical functions, including memory and learning. Glutamate acts both through ligand gated ion channels (ionotropic receptors) and second messenger (here G-protein) coupled (metabotropic) receptors. Ionotropic glutamate receptors can be divided into three groups: AMPA receptors, NMDA receptors, and kainate receptors.

Gamma-aminobutyric acid (GABA) is the main inhibitory neurotransmitter in the central nervous system. GABA is involved in 20 to 50 percent of brain synapses, depending on the brain area. There are three types of GABA receptors: $GABA_A$ and $GABA_C$ receptors, which are associated with chloride channels, and $GABA_B$ receptors, which are G-protein coupled (metabotropic) receptors. Binding of GABA to a $GABA_A$ receptor increases the permeability to chloride ion, which leads to hyperpolarization of the neuronal membrane and to increased inhibition. A $GABA_A$ receptor contains, for example, the following binding sites: GABA, benzodiazepine and barbiturate sites.

Anesthetics bind to specific, saturable binding sites (i.e. receptors) typically on the cell membrane. Effects of anesthetics are receptor-mediated. General anesthesia may be produced by different mechanisms: anesthetics may act at different receptors or they may act at different sites of the same receptor.

At present, most of the anesthetics act primarily through $GABA_A$-receptors. These drugs, also termed GABA agonistic agents, potentiate the actions of GABA causing hyperpolarization of the neuronal membrane. This action is common to barbiturates, propofol, etomidate, and steroid anesthetics, for example, and probably also to inhalational anesthetics.

Although most anesthesias are today conducted by GABA agonistic agents, another group of anesthetics is also used, which affects the N-methyl-D-aspartate (NMDA) receptors thereby attenuating excitatory neurotransmission. These drugs, also termed NMDA antagonists in this context, inhibit the actions of glutamate by blocking the NMDA receptors. This action is common to phencyclidine derivatives, like ketamine and S-ketamine, and to nitrous oxide and xenon, for example.

In addition to the EEG signal data, EMG signal data obtained from facial muscles (fEMG) of the forehead is used for monitoring purposes during anesthesia and intensive care. Recovering facial muscle activity is often the first indicator of the patient approaching consciousness. When this muscle activity is sensed by electrodes placed appropriately, it provides an early indication that the patient is emerging from anesthesia. Similarly, these electrodes can sense pain reactions when the anesthesia is not adequate due to inadequate analgesia. So, the EMG signals give an early warning of arousal and may also be indicative of inadequate analgesia.

An objective tool for assessing the level of anesthesia or sedation is disclosed in U.S. Pat. No. 6,801,803, which depicts a method and device for ascertaining the cerebral state of a patient. In this disclosure, a measure derived from EMG signal data enhances and confirms the determination of the hypnotic state made using EEG signal data. As the EMG data may be computed more frequently than the EEG data, it follows changes in the hypnotic state of the patient more rapidly. The combined indicator provided by the EEG signal data and EMG signal data may also be used for assessing the adequacy of anesthesia or the level of sedation.

At present, the processes utilizing raw EEG signal data for monitoring a patient under sedation or anesthesia utilize the fact that the frequencies of the EMG spectrum are above the frequencies of brain activities, whereby the EMG components can be separated by methods of signal processing or spectral analysis from the EEG signal components contained in the signal data. This causes no problems with the use of GABA agonistic agents, since the administration of GABA agonistic agents results in a more ordered EEG signal with spectral power concentrated onto the low frequencies. In this context, low frequencies refer to frequencies below about 20 Hz, while high frequencies refer to frequencies above about 20 Hz. A more ordered EEG signal will be the result also when NMDA antagonists are administered. However, NMDA antagonists produce both low and high frequency EEG activity, which confuses the operation of the present-day algorithms, since they cannot anymore separate high frequency EEG activity from EMG activity. Therefore, the level of hypnosis (or the depth of anesthesia) measured by such algorithms may not be reliable if high frequency EEG activity is induced.

The present invention seeks to alleviate or eliminate the above-mentioned drawback and to bring about a method by means of which the anesthetic state of a subject may be evaluated more accurately whenever drugs inducing high frequency EEG activity are used.

SUMMARY OF THE INVENTION

The present invention seeks to improve the reliability and thus also to extend the applicability of present-day mechanisms employing raw EEG signal data for monitoring the cerebral state of a subject. The invention further seeks to provide a method and apparatus, which are applicable for monitoring the level of hypnosis when NMDA antagonists are involved in producing anesthesia or sedation.

In the present invention, the operation of the monitoring process that calculates a variable indicative of the cerebral state of a subject is controlled according to whether or not substantial high frequency EEG activity is present in the signal data obtained from the subject. Substantial presence of the high frequency EEG activity here refers to activity which is beyond the normally negligible high frequency activity of the brain, and which may thus not be induced by normal brain function. If such activity is not present, the said variable may be calculated in a normal manner. However, if such high frequency EEG activity is present, the monitoring process is controlled to enter an operation mode in which the high EEG frequencies induced do not adversely affect the calculation of the variable. The said operation mode is here termed the NMDA mode. The control may be manual or automatic and the way the process is controlled depends on the underlying algorithm of the monitoring process. However, in a typical case of an entropy-based monitoring process the control process adjusts the frequency ranges over which the entropic indicators are calculated.

Thus one aspect of the invention is providing a method for monitoring the cerebral state of a subject. The method includes the steps of obtaining physiological signal data from a subject, the physiological signal data including EEG signal components, supplying the physiological signal data to a monitoring process configured to derive a state index from the physiological signal data, the state index being indicative of the cerebral state of the subject, and controlling the operation of the monitoring process according to whether at least one drug inducing high frequency EEG signal components is administered to the subject.

In one embodiment of the invention, the presence of the high frequency EEG activity is detected automatically, and the process is controlled to the NMDA mode whenever the said presence is detected.

Another aspect of the invention is that of providing an apparatus for monitoring the cerebral state of a subject. The apparatus includes first measurement means for obtaining physiological signal data from a subject, the physiological signal data including EEG signal components, monitoring means for deriving a state index from the physiological signal data, the state index being indicative of the cerebral state of the subject, and control means for controlling the operation of the monitoring means according to whether at least one drug inducing high frequency EEG signal components is administered to the subject.

The invention enables correct and reliable evaluation of the subject state whenever NMDA antagonists are used, together with or instead of GABA agonistic agents, to produce the anesthesia. The invention further enables efficient artifact rejection, since the control of the operation of the monitoring process allows the use of parameters optimized for artifact rejection.

A further aspect of the invention is that of providing a computer program product by means of which known patient monitoring devices may be upgraded and thus their applicability extended. The program product includes a first program code portion configured to receive a control instruction for controlling the operation of a monitoring process adapted to derive a state index indicative of the cerebral state of the subject and a second program code portion configured to control the operation of the monitoring process in response to the control instruction.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 to 5 in the appended drawings, wherein.

DETAILED DESCRIPTION OF THE INVENTION

Figure 1:
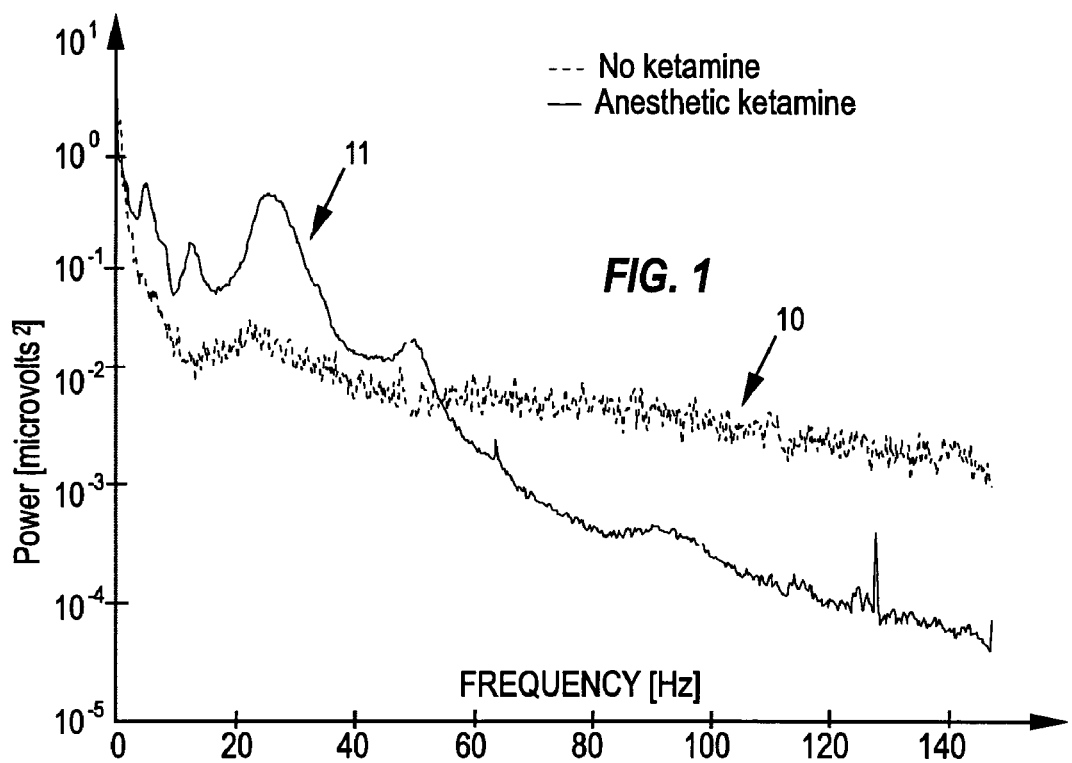
FIG. 1 illustrates the problem related to the use of NMDA antagonists.

FIG. 1 illustrates the problem related to the use of NMDA antagonists for producing anesthesia. The figure shows two power spectra analysed from S-ketamine anesthesia. The first power spectrum 10 is obtained when ketamine is not yet administered (i.e. the patient is still awake), while the second power spectrum 11 is obtained during ketamine anesthesia from the same patient. As can be seen from the figure, the spectrum above about 30 Hz is almost flat in the logarithmic scale when ketamine is not administered. During the ketamine anesthesia, the spectrum in turn shows a clear power increase in the frequency range below about 80 Hz, which is due to the high frequency EEG activity induced by ketamine.

Figure 2:
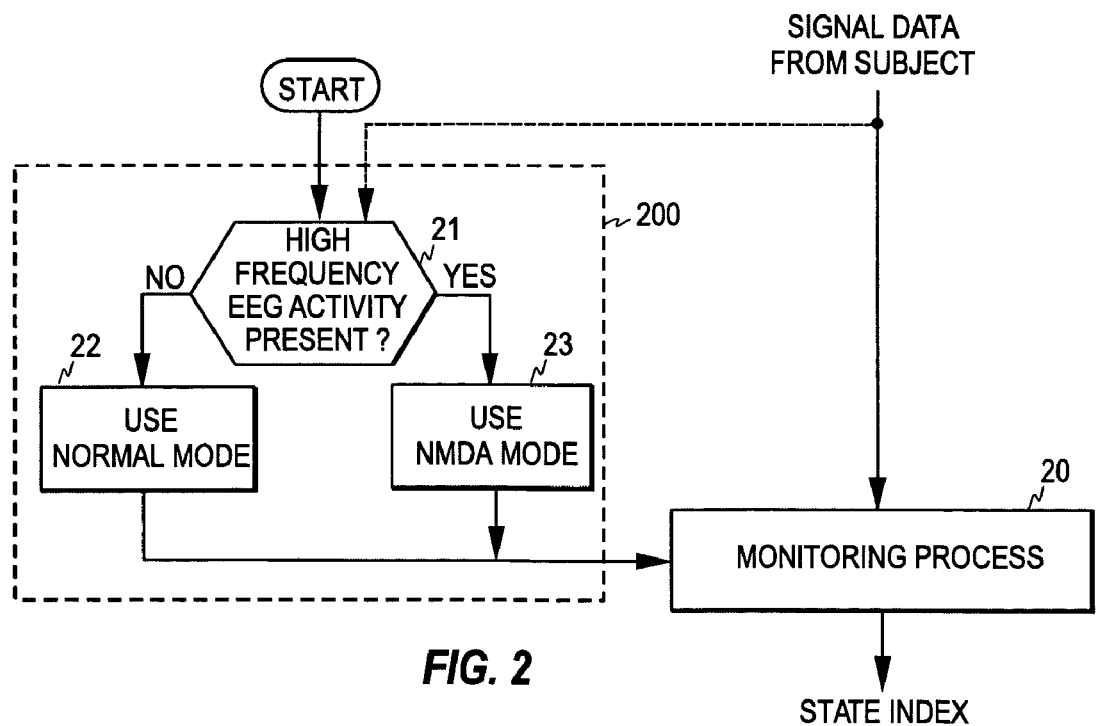
FIG. 2 is a flow diagram illustrating the general outline of the invention.

FIG. 2 illustrates the control principle of the present invention. In the present invention, the operation mode of the monitoring process 20 that calculates a measure of the level of hypnosis (or the depth of anesthesia) is controlled according to whether the signal data obtained from the subject includes high frequency EEG activity. Therefore, the embodiment of FIG. 2 comprises two parts: the said monitoring process 20, in which the said measure is calculated and a control process 200, which controls the operation of the monitoring process, i.e. the way in which the said measure is calculated. In the monitoring process, one of the present-day algorithms may be employed to estimate the anesthetic state of the subject, i.e. the level of hypnosis. The algorithm may be based on the calculation of the spectral entropy or the Bispectral Index (BIS™), for example, which are two well-known methods for evaluating the level of hypnosis (or the depth of anesthesia). The respective devices are marketed by GE Healthcare Finland Oy, Kuortaneenkatu 2, FIN-00510 Helsinki (Entropy™) and by Aspect Medical Systems, Inc., 141 Needham Street, Newton, Ma. 02464, U.S.A. (Bispectral Index, BIS™).

These algorithms typically yield a single variable indicative of the level of hypnosis or the depth of anesthesia. The said single variable is here termed the state index.

The internal operation (i.e. the operation mode) of the monitoring process is controlled by the control process 200 according to whether high frequency EEG activity is present in the signal data obtained from the subject. If this is the case, the monitoring process is controlled to assume the NMDA mode (steps 21 and 23). If high frequency EEG data is not present, the monitoring process assumes normal operation mode (steps 21 and 22). The control message instructing the monitoring process to switch the operation mode may be encoded in different ways. If the monitoring process knows the parameter values to be used in the both operation modes, the message may include only one bit that indicates the operation mode. However, the message may also indicate the new parameter values for the operation mode to be entered. As discussed below, the new parameter values are typically new bandwidth values for entropic indicators.

The control of the operation of the monitoring process may be automatic or manual. In case of automatic control, the signal data obtained from the subject is supplied to both the monitoring process and to the control process. In case of manual control, the anesthesiologist may switch the NMDA mode on, if he/she uses or intends to use NMDA antagonists to produce the anesthesia. The switching may be performed through any appropriate input means, such as a dedicated switch or the keyboard of a patient monitor.

To enable automatic control of the operation mode, the control process may automatically detect the presence of high frequency EEG activity in the signal data obtained from the subject. In one embodiment of the invention, this is carried out by examining the power of the signal data on two predetermined frequency bands. The first frequency band may be selected, for example, so that it covers both high end EEG frequencies and EMG frequencies, while the second frequency band may be selected so that it covers only EMG frequencies.

Figure 3:
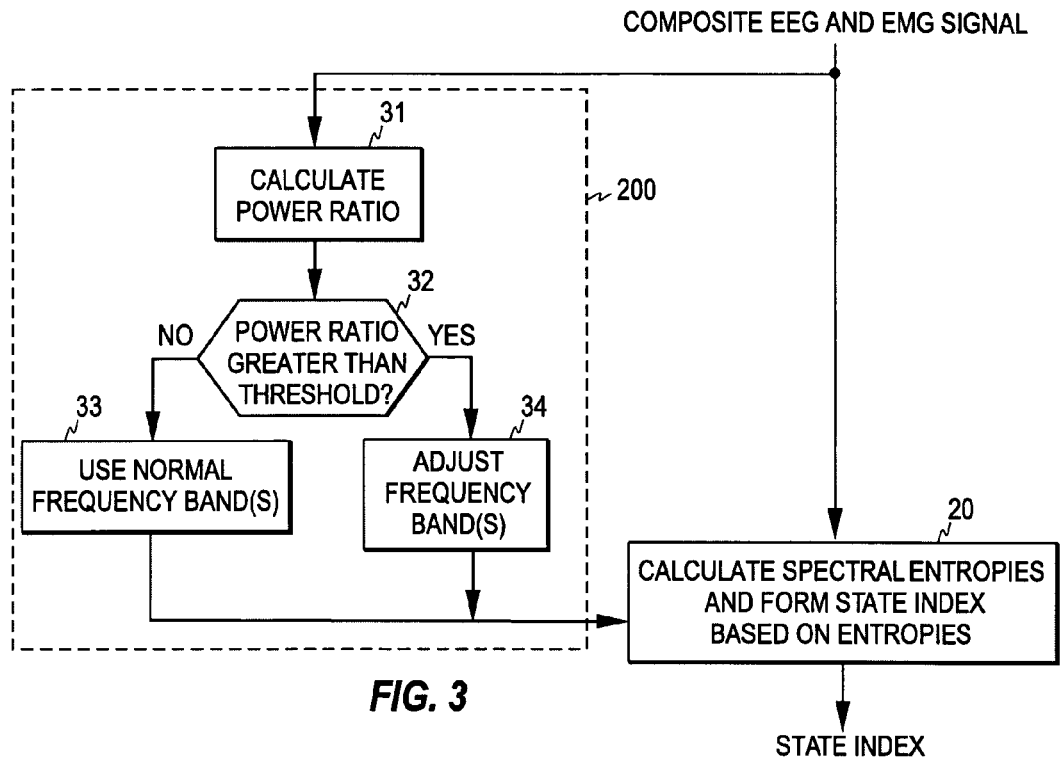
FIG. 3 is a flow diagram illustrating one embodiment of the method of the invention.

FIG. 3 illustrates an embodiment of the invention, in which the monitoring process 20 uses the spectral entropy of the signal data obtained from the subject to evaluate the depth of anesthesia, and the control process automatically detects the presence of high frequency EEG activity in the signal data. The digitized input signal, including both EEG and EMG components, is in this case supplied both to the monitoring process and to the control process. As is common in the art, the processing of the digitized input signal typically uses sets of sequential signal samples representing finite blocks of time, commonly termed "epochs". In the control process, a spectrum analysis is first performed at step 31, in which the ratio of the signal power (P1) on the above-mentioned first frequency band to the signal power (P2) on the above-mentioned second frequency band is calculated. The ratio (P1/P2) is then compared with a predetermined threshold value at step 32. If the ratio is greater than the threshold, the process decides that high frequency EEG activity is present, and the monitoring process is controlled to enter the NMDA mode. In this embodiment, where the monitoring process employs spectral entropies to evaluate the depth of anesthesia, the NMDA mode is entered by instructing the monitoring process to adjust the frequency bands used to calculate the entropic indicators, so that each indicator takes account of the presence of the high frequency EEG signal components. For example, a parameter indicative of only EEG entropy may in the NMDA mode be calculated based on wide frequency band extending up to about 145 Hz, while the said parameter may in the normal mode be calculated based on frequencies up to about 30 to 50 Hz. Similarly, if parameters specific to EMG are to be calculated in the NMDA mode, the lower limit of the respective frequency band increases accordingly so that the high frequency EEG components do not affect the result. This is discussed briefly in the following assuming that the entropy-based monitoring process is similar to the one used in the S/5 Entropy Module of the Applicant.

In the S/5 Entropy Module of the Applicant, which utilizes the mechanisms described in the above-mentioned U.S. Pat. No. 6,801,803, two entropic indicators termed State Entropy (SE) and Response Entropy (RE) are computed. State Entropy, which primarily reflects the cortical state of the patient, is computed over a frequency range from 0.8 Hz to 32 Hz, which corresponds to the EEG-dominant part of the spectrum. The Response Entropy, in turn, is computed over a frequency range from 0.8 Hz to 47 Hz, which also contains EMG frequencies. The difference between the State Entropy and the Response Entropy is then indicative of the EMG activation.

When this monitoring process is controlled to enter the NMDA mode, a single entropy value may be calculated over a frequency range wider than the frequency ranges of the normal mode. The upper limit of the said single frequency range may be increased to a certain first limit value, which is above 80 Hz and preferably around the above-mentioned value of 145 Hz. In this case, the single entropy value is indicative of the cortical state of the patient, because the frequency band used covers practically the whole EEG frequency range and EMG activation is negligible. When EMG activity increases again at the end of the anesthesia, the algorithm returns to normal operation mode and the State and Response Entropies are calculated in a conventional manner.

In the normal mode, the entropy-based monitoring process may thus be as disclosed in the above-mentioned U.S. Pat. No. 6,801,803, for example, which is in this context referred to for a more complete description of entropy-based monitoring processes. In one embodiment disclosed therein, the state index is calculated based on EEG entropy and EMG spectral power. As obvious from the above, if this embodiment is used in the NMDA mode, the EEG entropy is calculated over a frequency range extending up to an upper limit substantially higher than in the normal mode, such as 100 Hz, while the EMG spectral power may be calculated over a frequency range starting from a lower limit equal to the said upper limit.

Figure 4A:
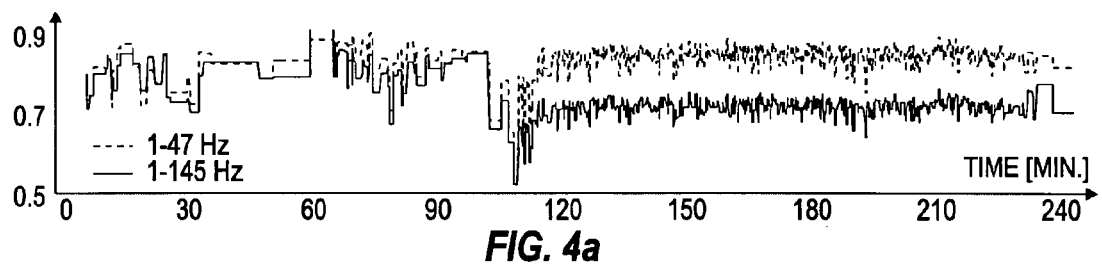
FIG. 4a to 4c illustrate the operation of one embodiment of the invention.
Figure 4B:
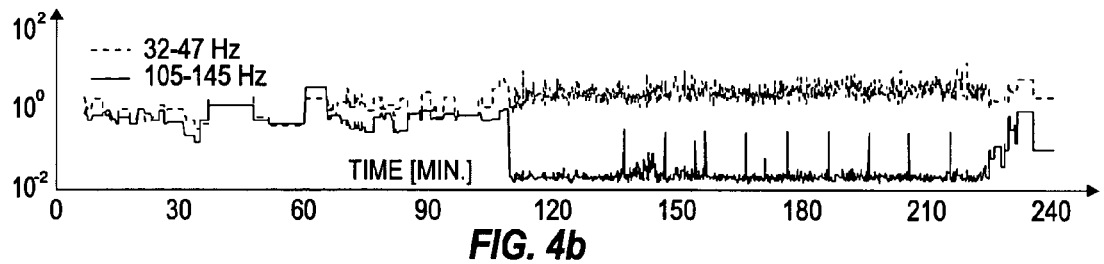
Figure 4C:
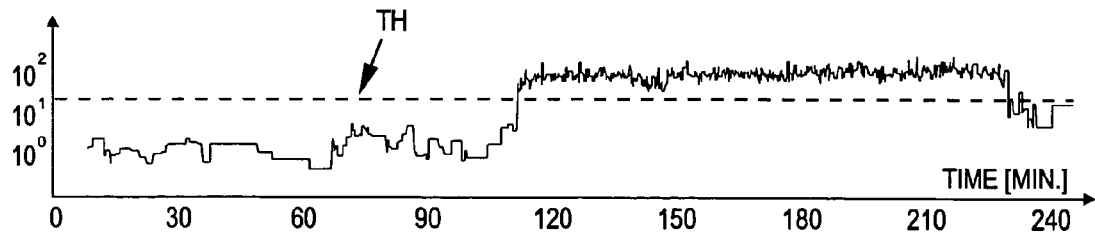

FIG. 4a to 4c illustrate the operation of the entropy-based monitoring process according to the embodiment of FIG. 3. FIG. 4a first illustrates the problem by showing spectral entropies measured from two frequency bands during ketamine anesthesia. In this example, one of the frequency bands is a narrow one, from 1 to 47 Hz, and the other is a wide one, from a 1 to 145 Hz. The subject is conscious for about the first 100 minutes and the entropies derived from both frequency bands are relatively high. At about 100 minutes, the subject is anesthetized with ketamine, and both entropies drop. However, quite soon after that the spectral entropy of the narrow band increases to the same level as in the conscious state, whereas the spectral entropy of the wide band remains low during the whole anesthesia. FIG. 4b presents the power values obtained at the same time from a first band covering both high end EEG frequencies and EMG frequencies and from a second band covering only EMG frequencies. In this example, the first band extends from 32 to 47 Hz and second band from 105 to 145 Hz. As is clearly observable from the figure, the power on the 105 to 145 Hz band, indicative of EMG activity, drops significantly when the patient is anesthetized. However, the power on the 32 to 47 Hz band slightly increases at the same time, because of the high frequency EEG activity produced by ketamine. FIG. 4c presents the ratio of power values of the above-mentioned bands and the threshold TH used to detect the high frequency EEG activity. Thus, in this example the above-mentioned first and second frequency bands, whose power ratio is calculated at step 31, are from 32 Hz to 47 Hz and from 105 Hz to 145 Hz, respectively. As can be seen, the above-described power ratio clearly indicates, when high frequency EEG activity is present in the signal data, thereby allowing the control process to control the operation of the monitoring process at the right moment of time.

Instead of entropy, the evaluation of the level of hypnosis may be based on another parameter that characterizes the amount of disorder or irregularity in the input signal data. However, currently the use of spectral entropy is deemed advantageous for this purpose due to the computational simplicity as compared to the other techniques available. Other possible quantifications that may be used include fractal spectrum analysis, Lempel-Ziv complexity, or bispectral or multispectral analyses. As a more detailed discussion of the various mathematical techniques available can be found in the above-referred U.S. Pat. No. 6,801,803, these methods are not discussed in detail in this context. However, the use of the bispectral index (BIS) is discussed briefly in the following.

The BIS involves the calculation of three subparameters, BetaRatio, SynchFastSlow, and Burst Suppression Ratio, and the resulting index is a combination of the three subparameters. Although the combining algorithm is unpublished and proprietary, it is known that the different subparameters are weighted according to their range of best performance and that different subparameters dominate the resulting BIS as the anesthesia increases. The SynchFastSlow subparameter corresponds to the logarithm of the ratio of the sum of all bispectral peaks in the frequency range from 0.5 to 47 Hz to the sum in the range from 40 to 47 Hz, while the BetaRatio gives the logarithm of the power ratio in the frequency ranges of 30 to 47 Hz and 11 to 20 Hz. The BetaRatio is weighted most heavily during light sedation. The SynchFastSlow subparameter itself is useful for tracking surgical anesthesia, but it seems obvious that the value of BetaRatio remains erroneously high if high frequency EEG activity produced by NMDA antagonists is present. Therefore, the BIS algorithm may also be controlled to enter the NMDA mode when drugs inducing high frequency EEG are administered. In one embodiment, this may be carried out by omitting the calculation of the BetaRatio or by substantially decreasing its weight when a drug inducing high frequency EEG activity is administered. In another embodiment, the control of the operation of the monitoring process may be carried out by replacing the above-mentioned frequency range of 30 to 47 Hz used in the calculation of the BetaRatio by a frequency range that is indicative of EMG activity but does not include the high EEG frequencies now induced. The lower limit of such a frequency band may be around 100 Hz, while the upper limit may be between 115 and 150 Hz, for example. One preferred modification of the BetaRatio for the NMDA mode is therefore the logarithm of the ratio $(P_{105-145})/(P_{11-20})$, for example, where $P_{A-B}$ is the sum of spectral power in the band extending from A Hz to B Hz. As the high frequency EEG activity induced by NMDA antagonists may also give rise to inconsistent behaviour of the SynchFastSlow parameter, the control of the operation of the monitoring process may further cover the adjustment of the SynchFastSlow subparameter. In this embodiment, at least one of the SynchFastSlow frequency ranges is adjusted to lie above high frequency EEG activity. One preferred modification of the SynchFastSlow for the NMDA mode is the logarithm of the ratio $(B_{0.5-93.5,0.5-93.5})/(B_{79.5-93.5,79.5-93.5})$ for example, where $B_{A-B,A-B}$ is the sum of bispectral peaks in the two dimensional frequency space covered by the corner frequencies A Hz and B Hz. The above-described detection mechanism for detecting the presence of high frequency EEG activity may also be used in connection with the BIS algorithm.

Figure 5:
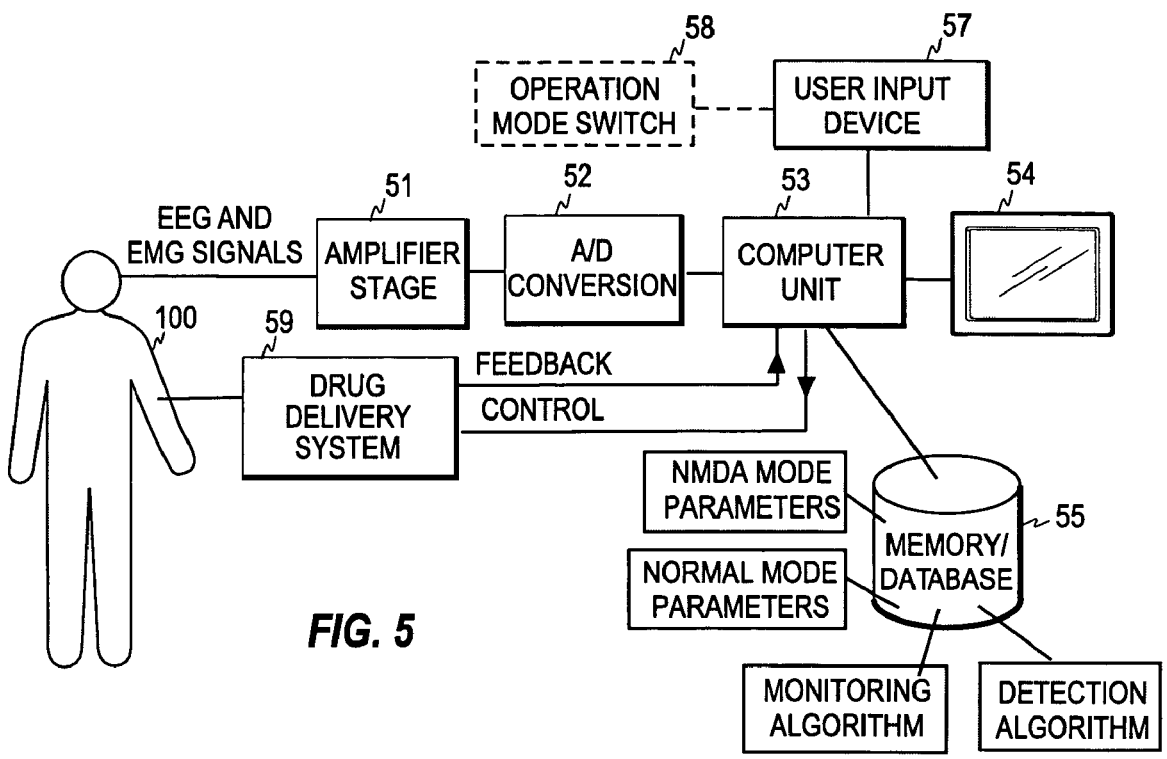
FIG. 5 illustrates one embodiment of the system according to the invention.

FIG. 5 illustrates one embodiment of the system or apparatus according to the invention. The physiological signal(s), i.e. the EEG and EMG signals, obtained from the sensors attached to the head of a patient 100 are supplied to an amplifier stage 51, which amplifies the signal(s) before they are sampled and converted into digitized format in an A/D converter 52. The digitized signals are supplied to a computer unit 53 which may comprise one or more processors.

The computer unit is provided with a memory or database 55, which may hold the digitized signal data obtained from the sensor(s), the monitoring algorithm, the detection algorithm for detecting the presence of high frequency EEG activity, and the parameters for the normal and NMDA modes of the monitoring process. The computer unit may produce the digitized time series needed and calculate the state index according to the monitoring algorithm in question. The computer unit may further detect the presence of high frequency EEG activity in the signal data and introduce the NMDA mode parameters whenever such presence is detected. The user may supply information, such as the NMDA mode parameters, through a user input device 57. If the operation mode is controlled manually, the same user input device, such as a keyboard, may be used to switch the operation mode of the monitoring algorithm. However, the user interface of the apparatus may also be provided with a dedicated operation mode switch 58 for manual control of the monitoring process.

The computer unit may display the results, i.e. the state index, through at least one monitor 54 connected to the computer unit.

The computer unit may further act as a controlling entity controlling the administration of the drugs from a delivery system 59 to the patient. The computer unit may also supply the index values to another computer unit or microprocessor (not shown), which then acts as the controlling entity controlling the drug delivery system. The said controlling entity may be provided with the control data needed for the administration, such as the pharmacodynamic and pharmacokinetic properties of the drugs to be administered. The drug delivery system may comprise separate delivery units for one or more drugs to be administered, such as delivery unit for an analgesic drug and/or a delivery unit for a hypnotic drug. The drug delivery system may inform the controlling entity when drug(s) inducing high frequency EEG activity are administered to the patient. The anesthesiologist may also control the operation of the drug delivery system through the user input device 57. For example, the anesthesiologist may supply the identifiers of the drug(s) to be administered through the user input device, such as a keyboard or a bar code reader, whereby the control unit is simultaneously informed if drug(s) inducing high frequency EEG activity is/are used.

In one embodiment, the presence of high frequency EEG data may be detected automatically even if the operation mode is controlled manually. In this case, the user is informed to switch the operation mode upon detection of high frequency EEG signal components, if the monitoring process is not in the NMDA mode when high frequency EEG signal components are detected. Any appropriate indicators, such as flashing lights, may be used to indicate that user action is required.

Although one computer unit or processor may perform the above steps, the processing of the data may also be distributed among different units/processors (servers) within a network, such as a hospital LAN (local area network). The apparatus of the invention may thus also be implemented as a distributed system. However, implementing the apparatus as a compact monitoring unit which may be movable with the patient allows the monitoring of the patient to be continued in a post anesthetic care unit, for example.

A conventional monitoring process, such as an entropy-based monitoring process, may also be upgraded to enable the relevant patient monitor to be used in connection with NMDA anesthesias. Such an upgrade may be implemented, for example, by delivering to the patient monitor a software module on a data carrier, such as a CD or a memory card. The software module, which may be provided with an interface to the memory storing the signal data measured by the patient monitor, may be a so-called plug-in module that adds the novel features of the invention to a conventional patient monitor or a new version of the software, which replaces the existing software of the patient monitor. A software module provided with an interface to the memory storing the signal data may detect whether a drug inducing high frequency EEG activity is administered to the patient and control the parameters of the monitoring process according to whether the use of such a drug is detected.

The software-based upgrade may also be such that it supports the manual control command given by the anaesthesiologist through a user input device of the patient monitor. In this case, the software controls the parameters of the monitoring process in the above-described manner in response to a control instruction given manually.

Although the invention was described above with reference to the examples shown in the appended drawings, it is obvious that the invention is not limited to these, but may be modified by those skilled in the art without departing from the scope and spirit of the invention. The detection mechanism of the invention may also be used in other applications for detecting high frequency EEG components and/or EMG components in signals which may comprise both components.

The invention claimed is:

1. A method for monitoring the cerebral state of a subject, the method comprising the steps of:
    obtaining physiological signal data from a subject, the physiological signal data including EEG signal components;
    supplying the physiological signal data to a monitoring process operating on a computer unit and configured to derive a state index from the physiological signal data, the state index being indicative of the cerebral state of the subject;
    determining in the computer unit whether a drug is being administered to the subject that induces high frequency EEG signal components; and
    modifying the operation of the monitoring process in the computer unit when the determining step determines at least one drug inducing high frequency EEG signal components is being administered to the subject.

2. A method according to claim 1, wherein the at least one drug is an NMDA antagonists.

3. A method according to claim 1, wherein the at least one drug belongs to a group including ketamine, S-ketamine, nitrous oxide, and xenon.

4. A method according to claim 1, wherein the determining step includes the sub-steps of
    calculating, based on the physiological signal data, signal power values on two predetermined frequency bands, whereby two signal power values are obtained;
    deriving a variable based on the two signal power values; and
    comparing the variable with a predetermined threshold value to detect whether the high frequency EEG signal components are substantially present in the physiological signal data.

5. A method according to claim 1, wherein the modifying step includes indicating at least one frequency band value to be used in the monitoring process in order to derive the state index.

6. A method according to claim 1, wherein the modifying step includes controlling the monitoring process to determine the state index as the entropy of the physiological signal data calculated over a frequency range extending from a frequency of about 0.5 Hz to a frequency which is above 80 Hz.

7. A method according to claim 1, wherein the determining step determines the drug administration through a user-operated actuator.

8. A method according to claim 1, further comprising a step of producing an indication informing whether the at least one drug is administered to the subject.

9. A method according to claim 8, wherein the producing step includes producing the indication, in which the indication is produced in a drug delivery system.

10. An apparatus for monitoring the cerebral state of a subject, the apparatus comprising:
    a measurement device positioned on a subject to obtain physiological signal data from the subject, the physiological signal data including EEG signal components;
    a monitoring device for deriving a state index from the physiological signal data, the state index being indicative of the cerebral state of the subject; and a computer unit for determining whether a drug is being administered to the patient that induces high frequency EEG signal components, wherein the computer unit modifies the operation of the monitoring device according to whether at least one drug inducing high frequency EEG signal components is administered to the subject.

11. An apparatus according to claim 10, wherein the computer unit is configured to:

monitor whether the high frequency EEG signal components are substantially present in the physiological signal data; and control the operation of the monitoring device upon detection of a substantial presence of the high frequency EEG signal components in the physiological signal data.

12. An apparatus according to claim 11, wherein the computer unit is further configured to calculate signal power values on two predetermined frequency bands, thereby to obtain two signal power values;

derive a variable based on the two signal power values; and compare the variable with a predetermined threshold value.

13. An apparatus according to claim 10, wherein the computer unit includes a user-operated actuator for controlling the operation of the monitoring means.

14. A computer program product, embodied on a computer readable medium, for monitoring the cerebral state of a subject, the computer program product comprising:

a first program code portion configured to receive a control instruction for controlling the operation of a monitoring process adapted to derive a state index indicative of the cerebral state of the subject;

a second program code portion configured to control the operation of the monitoring process in response to the control instruction; and a third program code portion configured to determine whether a drug inducing high frequency EEG signal components is being administered to the subject, wherein the second program code modifies the operation of the monitoring process upon detection of high frequency EEG signal components in the physiological data.

15. A method for monitoring the cerebral state of a subject, the method comprising the steps of:

obtaining physiological signal data from a subject, the physiological signal data including EEG signal components;

supplying the physiological signal data to a monitoring process operating on a computer unit and configured to derive a state index from the physiological signal data, the state index being indicative of the cerebral state of the subject;

monitoring whether high frequency EEG signal components are substantially present in the physiological signal data, the monitoring step comprising the sub-steps of:

calculating, based on the physiological signal data, signal power values on a first frequency band covering both EEG and EMG frequencies and on a second frequency band covering only EMG frequencies;

calculating a ratio of the calculated signal power in the first frequency band and the second frequency band; and comparing the ratio with a predetermined threshold value to detect whether the high frequency EEG signal components are substantially present in the physiological signal data; and modifying the operation of the monitoring process in the computer unit upon detecting that the high frequency EEG signal components are substantially present in the physiological signal data.

16. A method according to claim 15, wherein the first frequency band extends from a frequency of about 32 Hz to a frequency of about 47 Hz and the second frequency band extends from a frequency of about 105 Hz to a frequency of about 145 Hz.

* * * * *